United States Patent
Sachs et al.

(10) Patent No.: US 12,310,765 B2
(45) Date of Patent: May 27, 2025

(54) SYSTEM AND METHOD FOR MEASURING RADIOTRACER BOLUS MORPHOLOGY FOR QUANTITATIVE ANALYSIS

(71) Applicant: GE Precision Healthcare LLC, Wauwatosa, WI (US)

(72) Inventors: Jonathan Sachs, Haifa (IL); Raz Carmi, Haifa (IL)

(73) Assignee: GE PRECISION HEALTHCARE LLC, Wauwatosa, WI (US)

(*) Notice: Subject to any disclaimer, the term of this patent is extended or adjusted under 35 U.S.C. 154(b) by 225 days.

(21) Appl. No.: 18/138,862

(22) Filed: Apr. 25, 2023

(65) Prior Publication Data
US 2024/0358333 A1    Oct. 31, 2024

Related U.S. Application Data

(63) Continuation of application No. 17/518,696, filed on Nov. 4, 2021, now Pat. No. 11,707,237.

(51) Int. Cl.
*A61B 6/00* (2024.01)
*A61B 6/03* (2006.01)
*A61B 6/50* (2024.01)

(52) U.S. Cl.
CPC ............. *A61B 6/037* (2013.01); *A61B 6/486* (2013.01); *A61B 6/507* (2013.01); *G06T 2207/30104* (2013.01)

(58) Field of Classification Search
None
See application file for complete search history.

(56) References Cited

U.S. PATENT DOCUMENTS

| | | | |
|---|---|---|---|
| 9,872,664 B1* | 1/2018 | Jin | A61B 6/5282 |
| 2013/0261440 A1 | 10/2013 | Georgi et al. | |
| 2013/0320973 A1* | 12/2013 | Fenchel | A61B 6/5288 324/309 |
| 2015/0230763 A1 | 8/2015 | Nagai | |
| 2016/0180553 A1* | 6/2016 | Edic | A61B 5/055 382/107 |
| 2017/0270695 A1* | 9/2017 | Avinash | A61B 6/507 |
| 2022/0202963 A1 | 6/2022 | Collin et al. | |

* cited by examiner

*Primary Examiner* — Hoon K Song
(74) *Attorney, Agent, or Firm* — Fletcher Yoder, P.C.

(57) ABSTRACT

A computer-implemented method for determining a flow rate for a given vessel includes obtaining, via a processor, dynamic three-dimensional (3D) images of a subject utilizing nuclear medicine imaging. The method also includes obtaining, via the processor, injection parameters for a radiotracer bolus injected into the subject via an automated injector. The method further includes generating, via the processor, time activity curves (TACs) for the radiotracer bolus from the 3D images. The method even further includes estimating, via the processor, the flow rate for the given vessel based on a morphology of the one or more TACs and the injection parameters.

20 Claims, 16 Drawing Sheets

|  | TAC - Activity in artery | | | TAC - Activity/volume artery | | | Flow |
| --- | --- | --- | --- | --- | --- | --- | --- |
|  | Peak | Slope | FWHM | Peak | Slope | FWHM |  |
| Dilution | mul D |  |  | mul D |  |  | Div D |
| Narrowing | mul N |  |  |  | div N |  |  |
| Bifurcation |  | mul B |  |  | mul B |  | mul B |

FIG. 10

| No. | Process | Type | TAC - Activity in artery | | | TAC - Activity/volume artery | | | Flow |
|---|---|---|---|---|---|---|---|---|---|
| | | | Peak | Slope | FWHM | Peak | Slope | FWHM | |
| 1 | Injection of tracer into vein | Dilution | mul D1 | | | mul D1 | | | Div D1 |
| 2 | Transit through lungs/heart | Dilution | mul D2 | | | mul D2 | | | Div D2 |
| 3 | Abdominal aorta | Bifurcation | | mul B3 | | | mul B3 | | mul B3 |
| 4 | Renal artery | Bifurcation narrowing | mul N4 | mul B4 | | | mul B4 div N4 | | Mul B4 |

FIG. 12

SYSTEM AND METHOD FOR MEASURING RADIOTRACER BOLUS MORPHOLOGY FOR QUANTITATIVE ANALYSIS

CROSS-REFERENCE TO RELATED APPLICATIONS

This application claims is a continuation of U.S. patent application Ser. No. 17/518,696, entitled "SYSTEM AND METHOD FOR MEASURING RADIOTRACER BOLUS MORPHOLOGY FOR QUANTITATIVE ANALYSIS", filed Nov. 4, 2021, the contents of which are incorporated by reference in their entirety herein for all purposes.

BACKGROUND

The subject matter disclosed herein relates to medical imaging systems and, more particularly, to measuring radiotracer bolus morphology for quantitative analysis.

In nuclear medicine (NM) imaging, such as positron emission tomography (PET) or single photon emission computed tomography (SPECT), radiopharmaceuticals (e.g., radiotracer) are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

The determination of many quantitative metrics for an organ of interest requires knowing the activity, flow, and volume of a radiotracer bolus prior to entering the organ. However, surrogate metrics are often used to estimate the function. For example, the time activity curve (TAC) for a radiotracer bolus may be utilized to deconvolute other TACs and an integral calculated over the curve for Patlak analysis. However, dynamic NM SPECT images are typically planar and the accuracy of the measurements are impeded by various compounding factors (e.g., attenuation, poor resolution, scatter, etc.). Thus, utilizing surrogate metrics is less accurate. Dynamic PET 3D images are typically limited to the quantitative analysis of relatively slow radiotracer changes within tissues of interest.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a computer-implemented method for determining a flow rate for a given vessel is provided. The method includes obtaining, via a processor, dynamic three-dimensional (3D) images of a subject utilizing nuclear medicine imaging. The method also includes obtaining, via the processor, injection parameters for a radiotracer bolus injected into the subject via an automated injector. The method further includes generating, via the processor, time activity curves (TACs) for the radiotracer bolus from the 3D images. The method even further includes estimating, via the processor, the flow rate for the given vessel based on a morphology of the one or more TACs and the injection parameters.

In another embodiment, one or more non-transitory computer-readable media encoding one or more processor-executable routines is provided. The one or more routines, when executed by a processor, cause acts to be performed. The acts include obtaining dynamic three-dimensional (3D) images of a subject utilizing nuclear medicine imaging. The method also includes obtaining injection parameters for a radiotracer bolus injected into the subject via an automated injector. The method further includes generating time activity curves (TACs) for the radiotracer bolus from the 3D images. The method even further includes estimating the flow rate for the given vessel based on a morphology of the one or more TACs and the injection parameters.

In a further embodiment, a processor-based system is provided. The system includes a memory encoding one or more processor-executable routines, wherein the routines, when executed cause acts to be performed. The acts include obtaining dynamic three-dimensional (3D) images of a subject utilizing nuclear medicine imaging. The method also includes obtaining injection parameters for a radiotracer bolus injected into the subject via an automated injector. The method further includes generating time activity curves (TACs) for the radiotracer bolus from the 3D images. The method even further includes estimating the flow rate for the given vessel based on a morphology of the one or more TACs and the injection parameters. The system also includes a processor configured to access and execute the one or more routines encoded by the memory.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 10 is a chart depicting various terms from TACs for a given vessel that may be utilized in determining an overall morphology of a radiotracer bolus and a flow for the given vessel;

FIG. 12 is a chart depicting various terms from TACs for different regions of interest from a point of injection to the renal artery;

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present disclosure provides systems and methods for determining a flow rate for a given vessel utilizing direct measurement of the bolus morphology for quantitative analysis. The disclosed embodiments utilize the acquisition of dynamic images (e.g., three-dimensional (3D) images) utilizing NM imaging (e.g., PET imaging) in combination with an automatic injector for introducing a radiotracer into a subject (e.g., patient) at a predefined volume and rate. The dynamic 3D images and the injection parameters enable the activity and flow of the tracer through a given vessel to be analyzed based on a change in the morphology of one or more time activity curves (TACs) for the bolus. A multi-term vector, where the terms are based on the injection parameters and the morphology of the TACs, may be utilized to estimate the flow of a given vessel. Directly measuring the bolus provides a more accurate estimate of the flow in the given vessel.

Before turning to the figures, it should be noted that various dynamic contrast-enhanced CT and MRI techniques are known in the art. Such techniques are typically limited with regard to the goals of the present disclosure since the total duration of administrating the contrast agents is typically significantly larger than the required duration in NM. For example, NM radiotracer administration to the patient can be accomplished in less than 10 sec (due to the lower material volume). But sufficient CT or MRI contrast agent administration cannot be accomplished in less than 15 seconds due to causing too blurred of a TAC shape for the present purpose.

Figure 1:
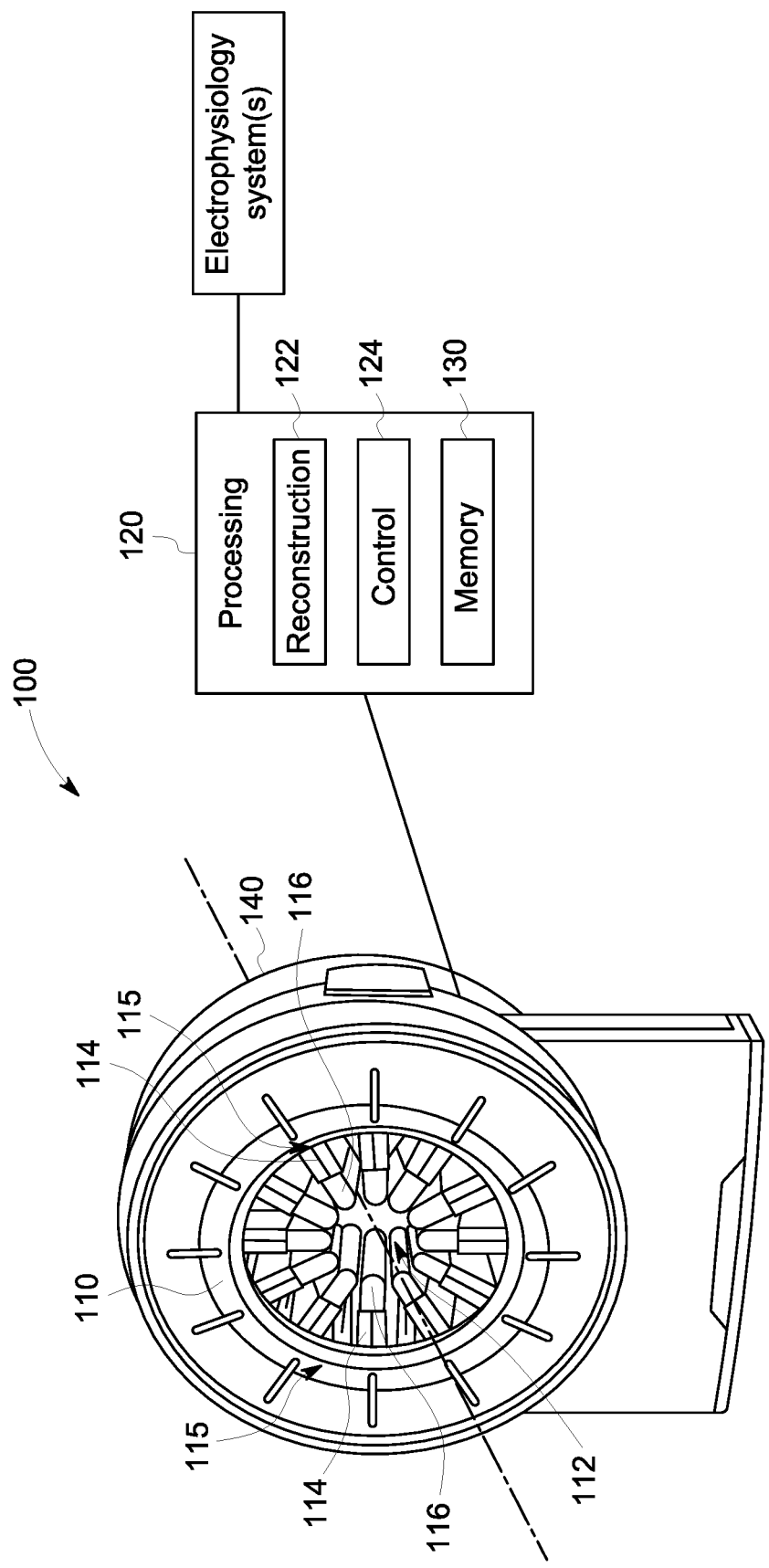
FIG. 1 is a schematic view of an embodiment of a nuclear imaging system, in accordance with aspects of the disclosed techniques.

FIG. 1 provides a schematic view of a NM multi-head imaging system 100 in accordance with various embodiments. Generally, the imaging system 100 is configured to acquire imaging information or data (e.g., photon counts) from an object to be imaged (e.g., a human patient) that has been administered a radiopharmaceutical. The depicted imaging system 100 includes a gantry 110 and a processing unit 120.

The gantry 110 defines a bore 112. The bore 112 is configured to accept an object to be imaged (e.g., a human patient or portion thereof). As seen in FIG. 1, a plurality of detector units 115 are mounted to the gantry 110. In the illustrated embodiment, each detector unit 115 includes an arm 114 and a head 116. The arm 114 is configured to articulate the head 116 radially toward and/or away from a center of the bore 112 (and/or in other directions), and the head 116 includes at least one detector, with the head 116 disposed at a radially inward end of the arm 114 and configured to pivot to provide a range of positions from which imaging information is acquired.

The detector of the head 116, for example, may be a semiconductor detector. For example, a semiconductor detector in various embodiments may be constructed using different materials, such as semiconductor materials, including Cadmium Zinc Telluride (CdZnTe), often referred to as CZT, Cadmium Telluride (CdTe), and Silicon (Si), among others. The detector may be configured for use with, for example, nuclear medicine (NM) imaging systems, positron emission tomography (PET) imaging systems, and/or single photon emission computed tomography (SPECT) imaging systems.

In various embodiments, the detector may include an array of pixelated anodes, and may generate different signals depending on the location of where a photon is absorbed in the volume of the detector under a surface of the detector. The absorption of photons from certain voxels corresponding to particular pixelated anodes results in charges generated that may be counted. The counts may be correlated to particular locations and used to reconstruct an image.

In various embodiments, each detector unit 115 may have a corresponding stationary field of view (FOV) that is oriented toward the center of the bore 112. Furthermore, each detector unit 115 in the illustrated embodiment is configured to acquire imaging information over a sweep range of the given detector unit 115. Thus, each detector unit 115 may collect information over a range larger than a field of view defined by a stationary detector unit. It may be noted that, generally, the sweeping range over which a detector unit 115 may potentially pivot may be larger than the corresponding FOV during acquisition. In some cameras, the sweeping range that a detector may pivot may be unlimited (e.g., the detector may pivot a full 360 degrees), while in some embodiments the sweeping range of a detector may be constrained, for example over 180 degrees (from a −90 degree position to a +90 degree position relative to a position oriented toward the center of the bore). The gantry 110 may be rotatable to different positions, with the detector units 115 rotating with the gantry 110. For example, with the gantry 110 in a first position, the individual detector units 115 may be swept to acquire a first set or amount of imaging information. Then, the gantry 110 may be moved to a second position (e.g., rotated to a new position, with the detector units 115 moving or rotating with the gantry 110). With the gantry 110 in the second position, the individual detector units 115 may be swept again to acquire a second set or amount of imaging information.

In some embodiments, the system 100 further includes a CT (computed tomography) detection unit 140. The CT detection unit 140 may be centered about the bore 112. Images acquired using both NM and CT by the system are accordingly naturally registered by the fact that the NM and CT detection units are positioned relative to each other in a known relationship. A patient may be imaged using both CT and NM modalities at the same imaging session, while remaining on the same bed, which may transport the patient along the common NM-CT bore 112. In certain embodiments, during imaging, the patient may have sensors coupled to them to monitor one or more physiological parameters (e.g., electrical heart activity (e.g., via an electrocardiogram (ECG)), respiration rate, etc.).

With continued reference to FIG. 1, the depicted processing unit 120 is configured to acquire imaging information or data (e.g., photon counts) via the detector units 115. In various embodiments the imaging information includes focused imaging information and background imaging information. The focused imaging information corresponds to a focused region, and the background imaging information corresponds to tissues surrounding the focused region. As used herein, both the focused region and surrounding tissue may be used for imaging and/or diagnostic purposes; however, the focused region may be more pertinent or useful for diagnostic purposes, and, accordingly, more imaging information is acquired for the focused region than for the surrounding tissue.

In various embodiments the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors, FPGA's, ASIC's and/or computers, which may be integrated in a common housing or unit, or which may be distributed among various units or housings (e.g., one or more aspects of the processing unit 120 may be disposed onboard one or more detector units, and one or more aspects of the processing unit 120 may be disposed in a separate physical unit or housing). The processing unit 120, for example, may determine acquisition range boundaries for focused and background regions, control the detector heads to acquire desired amounts of focused and background information, and reconstruct an image as discussed herein. It may be noted that operations performed by the processing unit 120 (e.g., operations corresponding to process flows or methods discussed herein, or aspects thereof) may be sufficiently complex that the operations may not be performed by a human being within a reasonable time period. For example, identifying boundaries of acquisition ranges, providing control signals to detector units, reconstructing images, or the like may rely on or utilize computations that may not be completed by a person within a reasonable time period.

In the illustrated embodiment, the processing unit 120 includes a reconstruction module 122, a control module 124, and a memory 130. The depicted reconstruction module 122 is configured to reconstruct an image. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein.

In certain embodiments, one or more electrophysiological systems 132 (e.g., cardiac monitoring system, respiratory monitoring system, etc.) may be coupled to the processing unit 120. In certain embodiments, the processing unit 120 and the electrophysiological systems 132 may be coupled to a controller (e.g., having memory and processing circuitry) separate from both the imaging system 100 and the electrophysiological systems 132. The electrophysiological systems 132 (via sensors) may enable the monitoring of cardiac and/or respiratory cycle data. In addition, dynamic image acquisition (e.g., utilizing the imaging system 100) may include synchronizing or gating a sequence of image acquisition relative to measuring cardiac and/or respiratory signals by the one or more electrophysiology systems 132.

The following techniques are described with regard to determining renal plasma (or blood) flow and/or glomerular filtration rate. Renal plasma flow is the volume of plasma flowing through the kidney each minute. Glomerular filtration rate (GFR) is the volume of plasma filtered by the kidney each minute. In this example, a given vessel as discussed below may be the renal artery. The techniques discussed herein may be applied to any given vessel that quantitative analysis of flow is desired.

Figure 2:
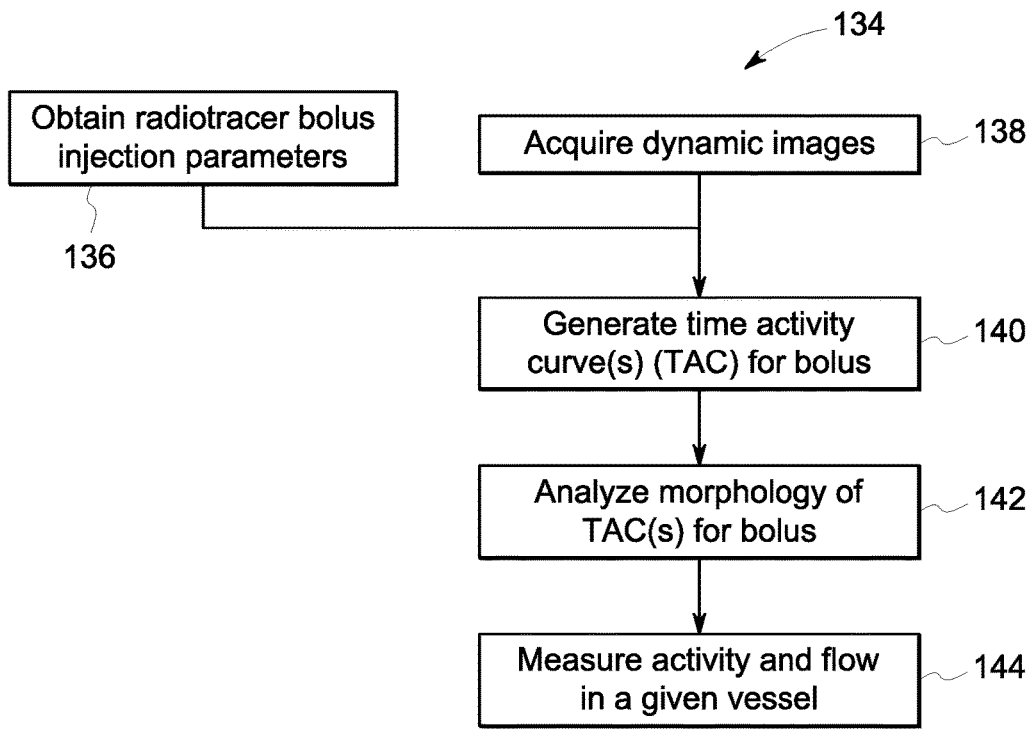
FIG. 2 is a method for determining a flow rate for a given vessel, in accordance with aspects of the disclosed techniques.

FIG. 2 is a method 134 for determining a flow rate for a given vessel. One or more steps of the method 134 may be performed by the NM multi-head imaging system (e.g., processing unit 120 in FIG. 1) and/or another processing unit. One or more of the steps of the method 134 may be performed at the same time and/or in a different order from that depicted in FIG. 2. The method 134 includes obtaining radiotracer bolus injection parameters relating to a radiotracer bolus injected into a subject via an automatic injector (e.g., in less than 10 seconds) (block 136). The injection parameters may include the dose of the radiotracer bolus injected, volume of the radiotracer bolus injected, and/or rate of injection of the radiotracer bolus. The method 134 also includes acquiring dynamic images (e.g., 3D images) utilizing a NM imaging system such as a SPECT or PET imaging system (block 138). The dynamic images include within them all areas (including the given vessel) of the subject that may be utilized for generating TACs for the radiotracer bolus.

The method 134 further includes generating one or more TACs from the 3D images (block 140). The TACs may include TACs for activity of the radiotracer bolus in a vessel. The TACs may also include TACs for activity of the radiotracer bolus in the vessel divided by a volume in the vessel. The TACs may be generated for a number of regions of interest. One region of interest has the given vessel. The other regions of interest are located upstream of the region of interest having the given vessel. For example, the region of interest having the given vessel may be the renal artery. The upstream regions of interest may be the site (e.g., vein) of injection, transit through lungs/heart, and/or abdominal artery.

The method 134 even further includes analyzing the morphology (e.g., shape or characteristics of the TACs such as peak, slope, full width half maximum (FWHM), etc.) of the one or more TACs for the radiotracer bolus for the regions of interest (block 142). The method 134 still further includes measuring activity and/or flow rate in the vessel (block 144). Measuring the activity includes estimating the activity and/or flow rate based on the morphology of the one or more TACs and the injection parameters. Estimating the activity or flow rate includes utilizing a multi-term vector, where the terms of the vectors are based on the morphology of the TACs and the injection parameters. As described in greater detail below, the multi-term vector takes into account dilution of the radiotracer bolus, narrowing of a vessel, and bifurcation of a vessel.

Figure 3:
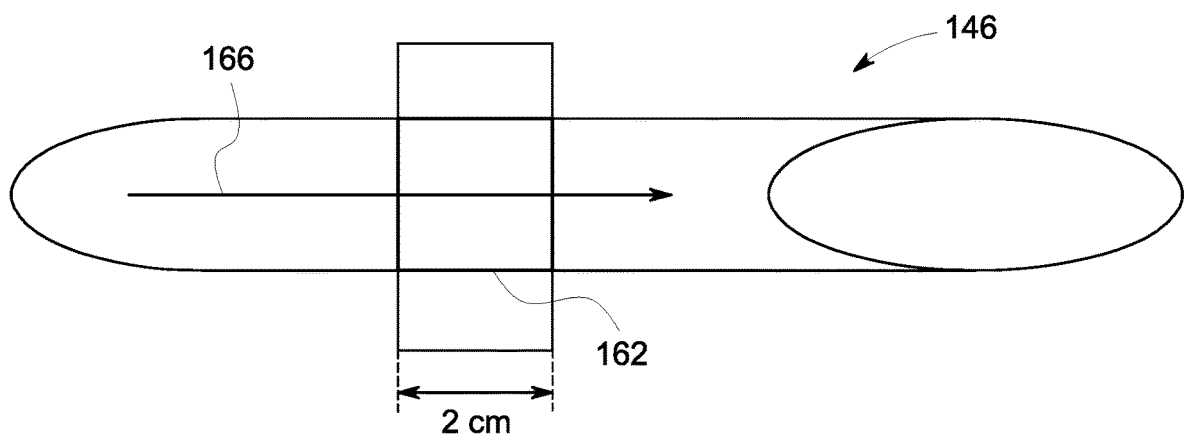
FIG. 3 is a schematic diagram of a vessel.
Figure 4:
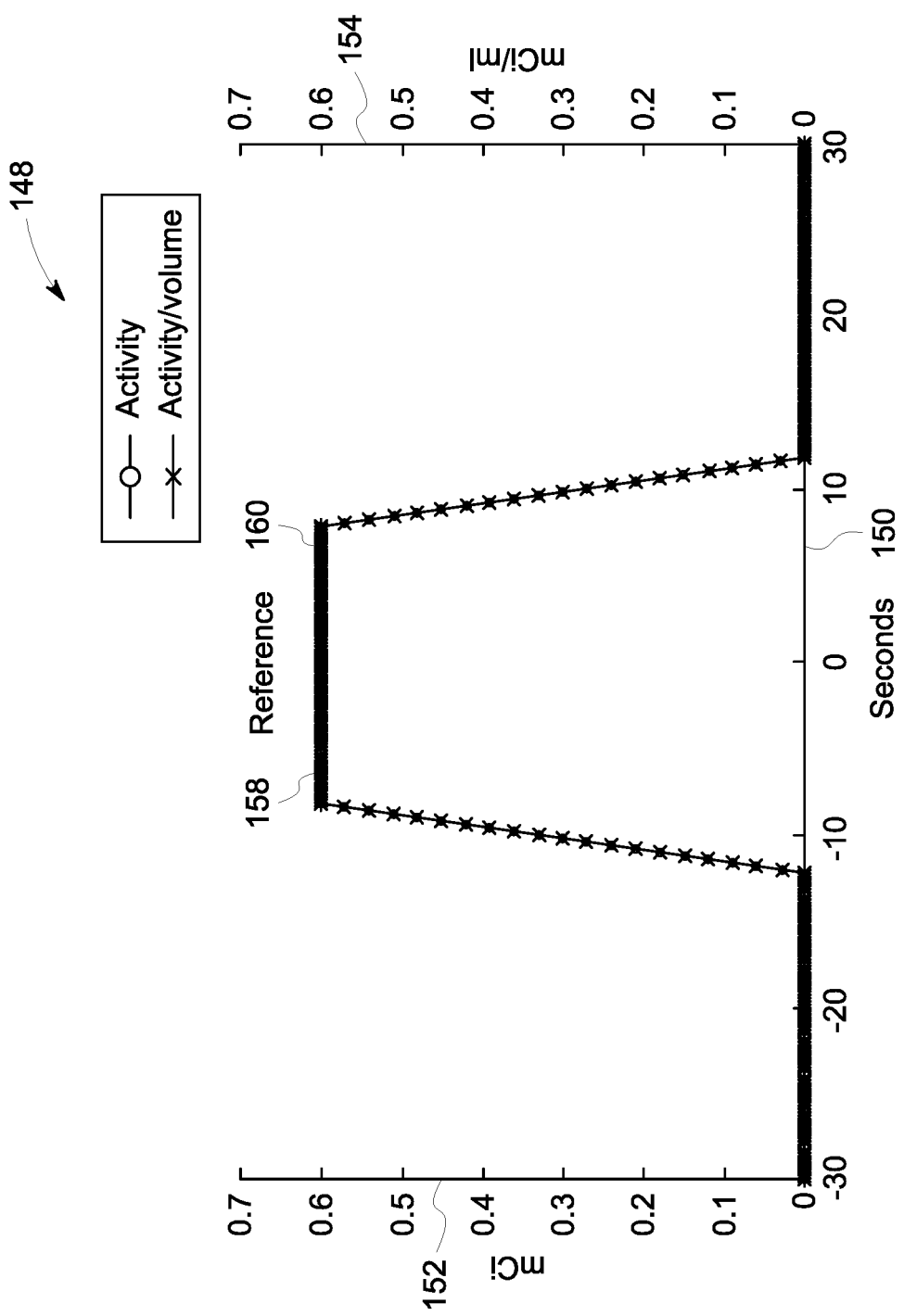
FIG. 4 is a graphical representation of reference time activity curves (TACs)
Figure 5:
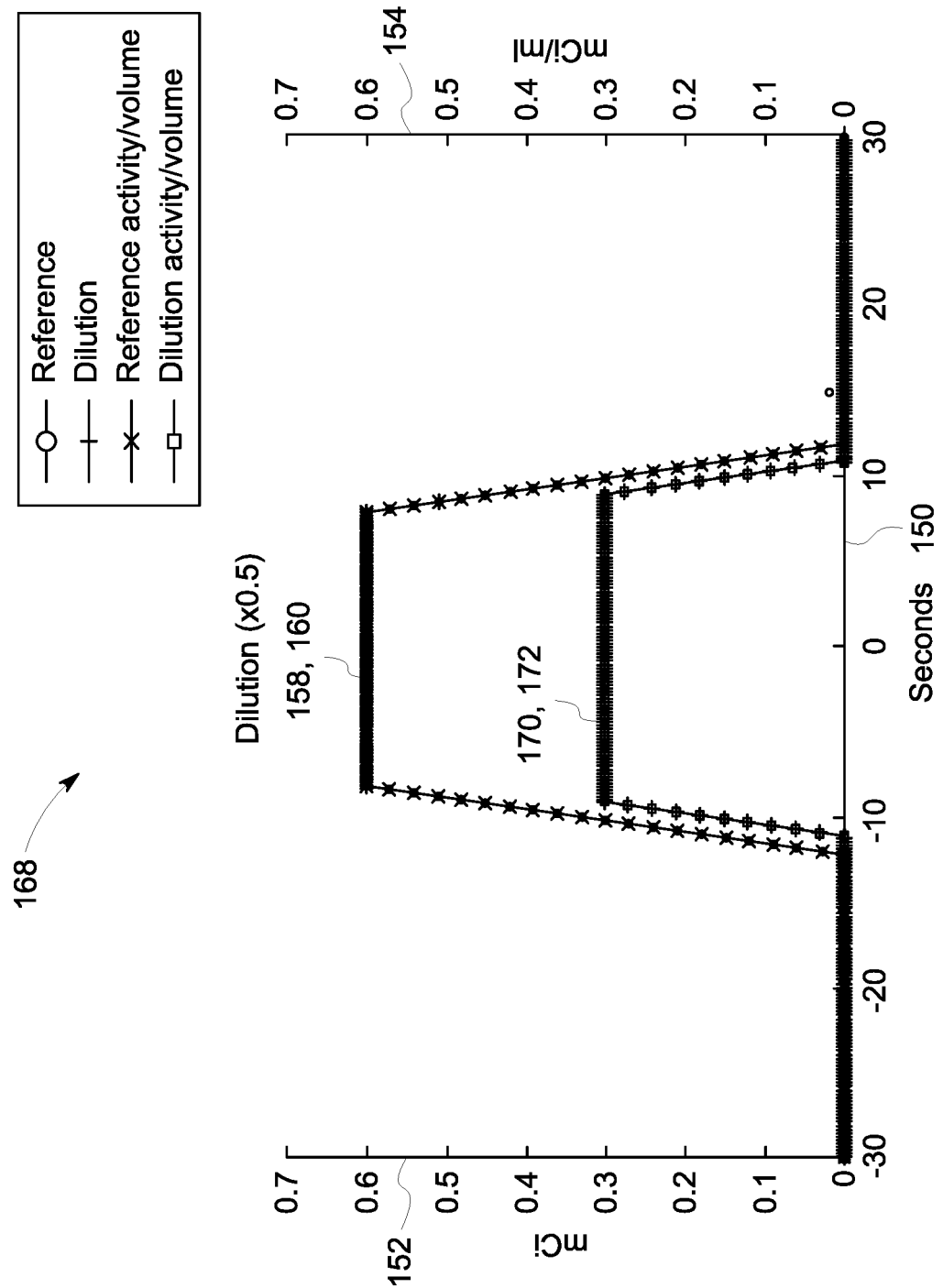
FIG. 5 is a graphical representation of TACs where dilution occurs versus reference TACs.
Figure 7:
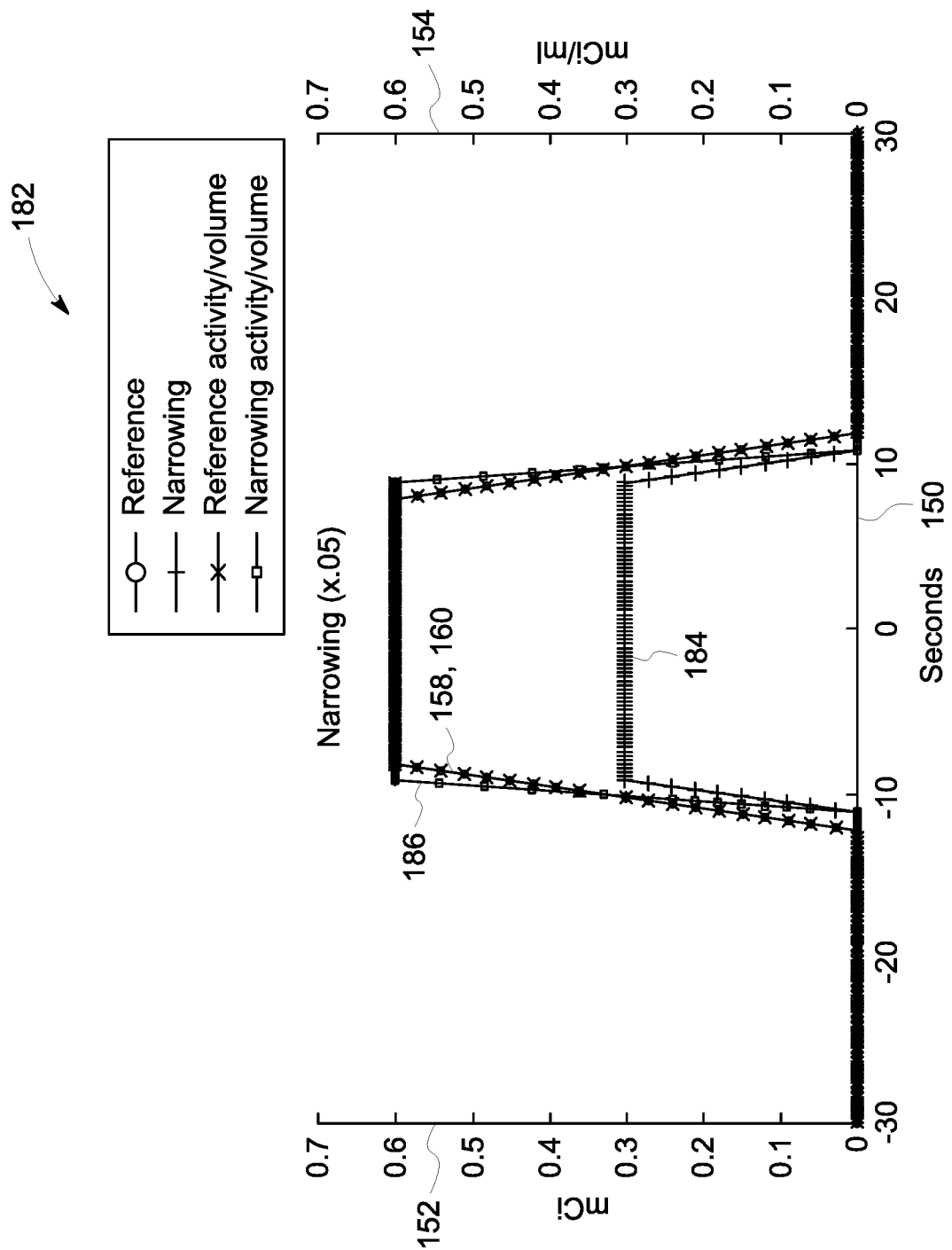
FIG. 7 is a graphical representation of TACs where narrowing occurs versus reference TACs.
Figure 9:
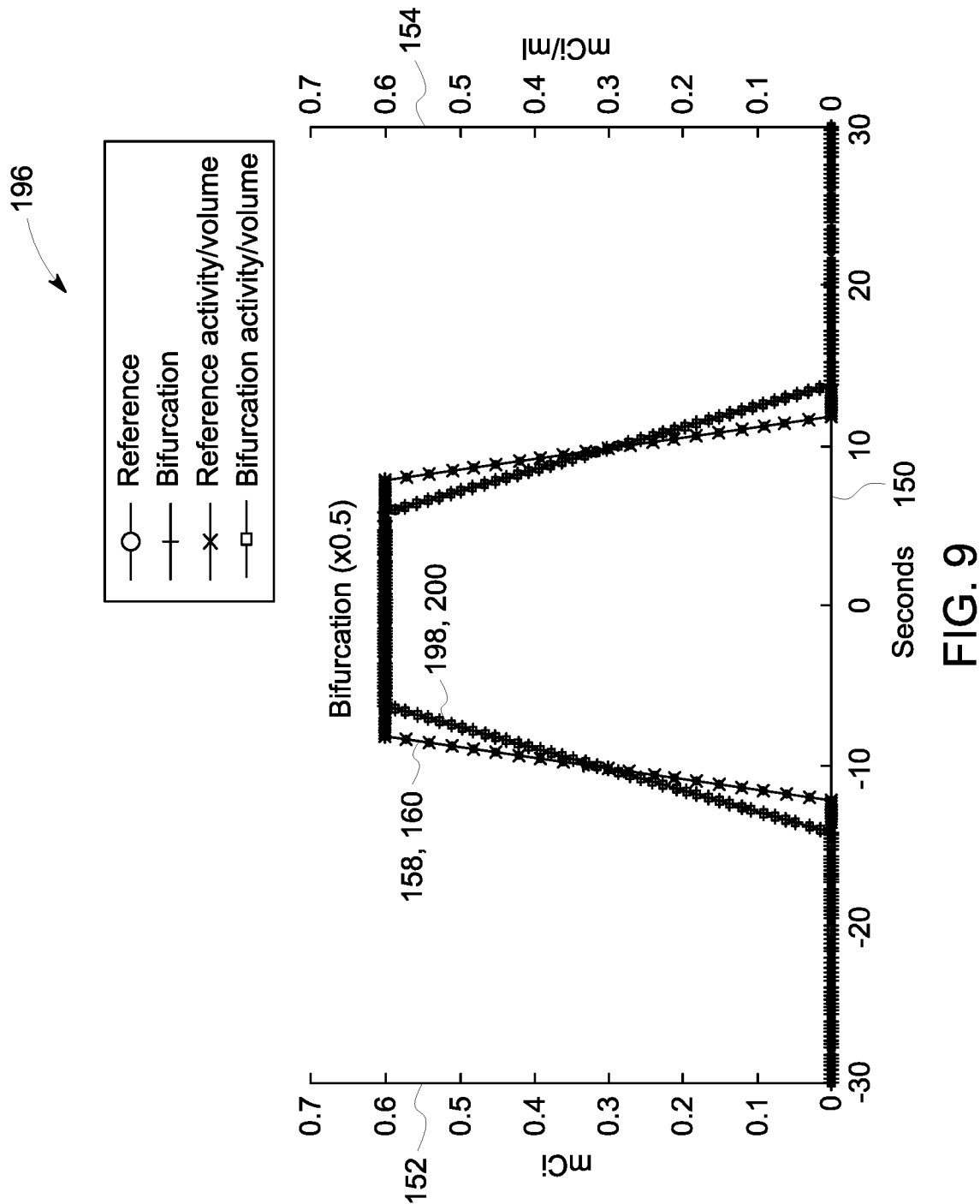
FIG. 9 is a graphical representation of TACs where bifurcation occurs versus reference TACs.

A number of factors may affect the shape of the TACs of the radiotracer bolus. One factor is dilution (including convolution due to bolus transit through an organ). Dilution is caused by adding blood to the bolus that increases the overall flow (e.g., when injecting the radiotracer bolus into a vein or when vessels merge into one vessel). Another factor is variations in the diameter of vessels (e.g., narrowing). A further factor is branching or bifurcation of a vessel. FIGS. 5, 7, and 9 illustrate the effects of these parameters on the TAC morphology. FIG. 3 is a schematic diagram of a vessel 146 (e.g., artery) for reference in discussing the TACs in FIG. 4. FIG. 4 is a graphical representation 148 of reference TACs (i.e., absent of dilution, narrowing, and bifurcation). The graphical representation 148 includes an X-axis 152 representing time (in seconds), a left Y-axis 154 representing activity (millicuries (mCi)), and a right Y-axis 156 representing activity divided by volume (mCi/mL). These same axes 152, 154, 156 are included in FIGS. 5, 7, and 9. Plots 158, 160 (which overlap) represent a TAC for activity of a radiotracer bolus in a reference region of interest or volume of interest 162 (see FIG. 3) of the vessel 146 over time and a TAC for activity of a radiotracer bolus in the reference region of interest 162 divided by a volume in the region of interest 162 (see FIG. 3) over time, respectively. Flow through the reference region of interest 162 of the vessel 146 is indicated by arrow 166 in FIG. 3. The TACs 158, 160 serve as reference TACs in FIGS. 5, 7, and 9. The following parameters relate to the determining the reference TACs 158, 160: injected dose was 3 mCi, the volume of injection was 5 mL, the duration of injection was 20 seconds, the length of the reference region of interest 162 was 2 cm, and the volume of the artery under the region of interest 162 was 1 mL, and the flow 166 in the region of interest 162 was 0.25 mL/sec.

FIG. 5 is a graphical representation 168 of TACs where dilution occurs versus reference TACs. Plots 170, 172 (which overlap) represent a TAC for activity of a radiotracer bolus in a region of interest or volume of interest in a vessel over time where dilution occurs (by a factor ×0.5) and a TAC for activity of a radiotracer bolus in the region of interest in the vessel where dilution occurs divided by a volume in the region of interest over time, respectively. The following parameters relate to the determining the TACs 170, 172: injected dose was 3 mCi, the volume of injection was 10 mL (twice the reference volume of injection), the duration of injection was 20 seconds, the length of the region of interest was 2 cm, and the volume of the artery under the region of interest was 1 mL, and the flow in the region of interest was 0.50 mL/sec (twice the reference flow). As depicted in the graphical representation 168, a height (i.e., activity and activity/volume) of the TACs 170, 172 is reduced in half compared to the reference TACs 158, 160.

Figure 6:
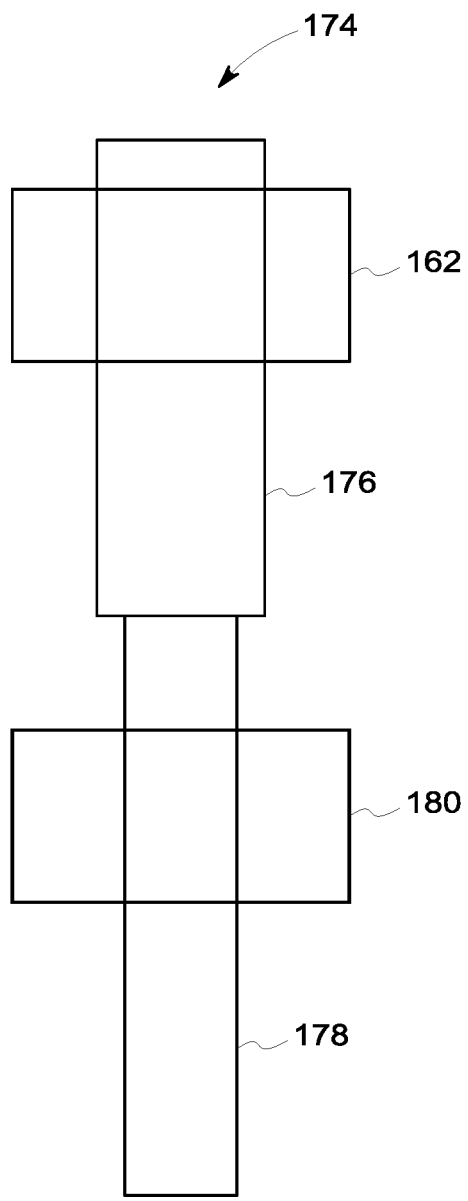
FIG. 6 is schematic diagram of a narrowing of a vessel.

FIG. 6 is a schematic diagram illustrating a narrowing of a vessel 174 (e.g., artery). The vessel 174 includes a wider portion 176 having the reference region of interest 162 and a narrower portion 178 having a region of interest 180 for analyzing the effects of narrowing (shown in FIG. 7). FIG. 7 is a graphical representation 182 of TACs where narrowing occurs versus reference TACs. Plots 184, 186 represent a TAC for activity of a radiotracer bolus in the region of interest or volume of interest 180 in the vessel 174 over time where narrowing occurs (by a factor ×0.5) and a TAC for activity of a radiotracer bolus in the region of interest 180 in the vessel 174 where narrowing occurs divided by a volume in the region of interest 180 over time, respectively. The following parameters relate to the determining the TACs 184, 186: injected dose was 3 mCi, the volume of injection was 5 mL, the duration of injection was 20 seconds, the length of the region of interest 180 was 2 cm, and the volume of the artery under the region of interest 180 was 0.5 mL, and the flow in the region of interest 180 was 0.25 mL/sec (same as the reference flow). As depicted in the graphical representation 182, a height (i.e., activity) of the TAC 184 is reduced in half compared to the reference TAC 158. A height (i.e., activity/volume) of the TAC 186 is the same as the reference TAC 160. The slope of the TAC 186 is two times greater than the slope of the reference TAC 160.

Figure 8:
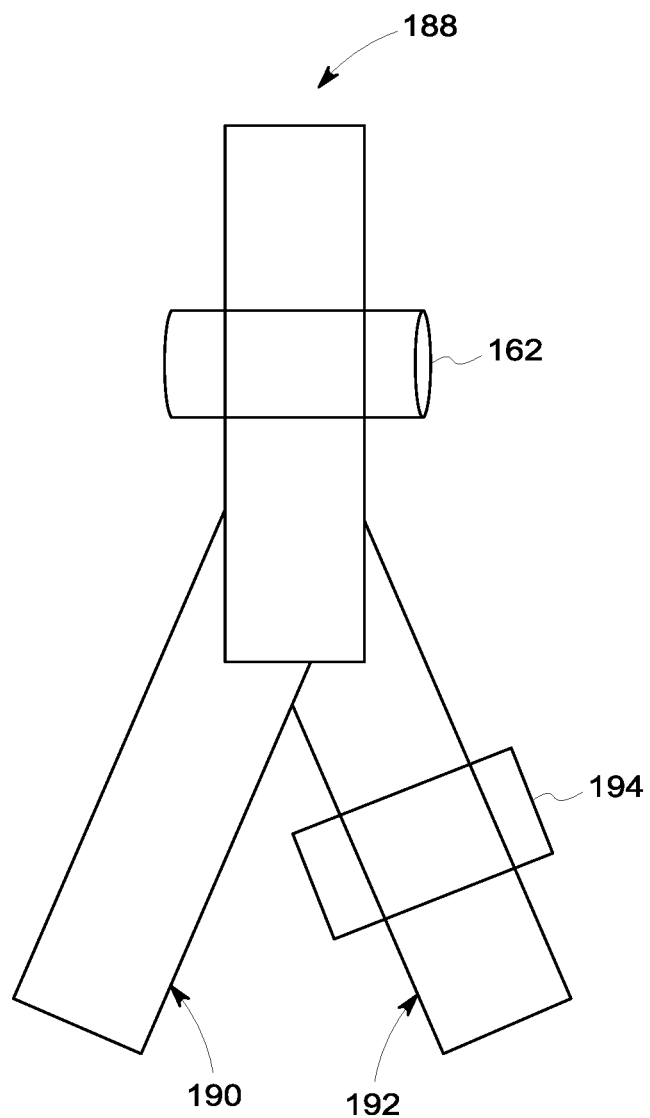
FIG. 8 is a schematic diagram of bifurcation of a vessel.

FIG. 8 is a schematic diagram illustrating a vessel 188 (e.g., artery) bifurcating into vessels 190, 192. The vessel 188 includes the reference region of interest 162. The vessel 192 includes a region of interest 194 for analyzing the effects of bifurcation (shown in FIG. 9). FIG. 9 is a graphical representation 196 of TACs where bifurcation occurs versus reference TACs. Plots 198, 200 (which overlap) represent a TAC for activity of a radiotracer bolus in the region of interest or volume of interest 194 in the vessel 192 which bifurcated from the vessel 188 (with a bifurcation factor of ×0.5) and a TAC for activity of a radiotracer bolus in the region of interest 194 in the vessel 192 by a volume in the region of interest 192, respectively. The following parameters relate to the determining the TACs 198, 200: injected dose was 1.5 mCi (half the reference dose), the volume of injection was 2.5 mL (half the reference volume of injection), the duration of injection was 20 seconds, the length of the region of interest 192 was 2 cm, and the volume of the artery under the region of interest 180 was 1 mL, and the flow in the region of interest 192 was 0.125 mL/sec (one-fourth the reference flow). As depicted in the graphical representation 196, a height (i.e., activity and activity/volume) of the TACs 198, 200 is the same as the reference TACs 158, 160. A slop of the TACs 198, 200 is half that of the reference TACs 158, 160.

From the TACs under various conditions (e.g., dilution, narrowing, and bifurcation), terms for a multi-term vector may be determined for calculating a flow within a given vessel. FIG. 10 illustrates a chart 202 depicting various terms from TAC for activity in a given vessel over time and TAC for activity divided by volume in the given vessel over time that may be utilized (as derived from FIGS. 5, 7, and 9) in determining an overall morphology of a radiotracer bolus and a flow for a given vessel. D, N, and B represent dilution, narrowing, and bifurcation, respectively. The abbreviations mul and div stand for multiply and divide, respectively, and indicate how the terms will be utilized in determining flow for the given vessel. Non-italicized letters represent letters are derived from the TAC for activity and italicized letters represent letters are derived from the TAC for activity divided by volume. P stands for peak, S stand for slope, and FWHM stands full width half maximum. The following equations assume the dose of the radiotracer bolus was injected into an end of the vessel (e.g., artery) proceeded and followed by water. The TAC measured over a vessel represents a combination of dilution (D), narrowing (N) and bifurcation (B) relative to a reference TAC measured upstream to the measured vessel. The magnitude of D, N and B can be determined by measuring the peak (P) and slope(S) of the vessel's TAC (for activity) and the peak (P) and slope(S) of the vessel's activity/volume TAC. More specifically, $P/P_{ref}$ equals N times D. $S/S_{ref}$ equals B. $P/P_{ref}$ equals D. $S/S_{ref}$ equals N times D. Flow equals (B/D) times flow of the reference ($Flow_{ref}$). N and D cannot be distinguished using the TACs. D can be found by determining the activity per volume (P/V), where V is the volume of the vessel under the region of interest. More specifically, D equals ($P/P_{ref}$) times ($V_{ref}/V$).

Figure 11:
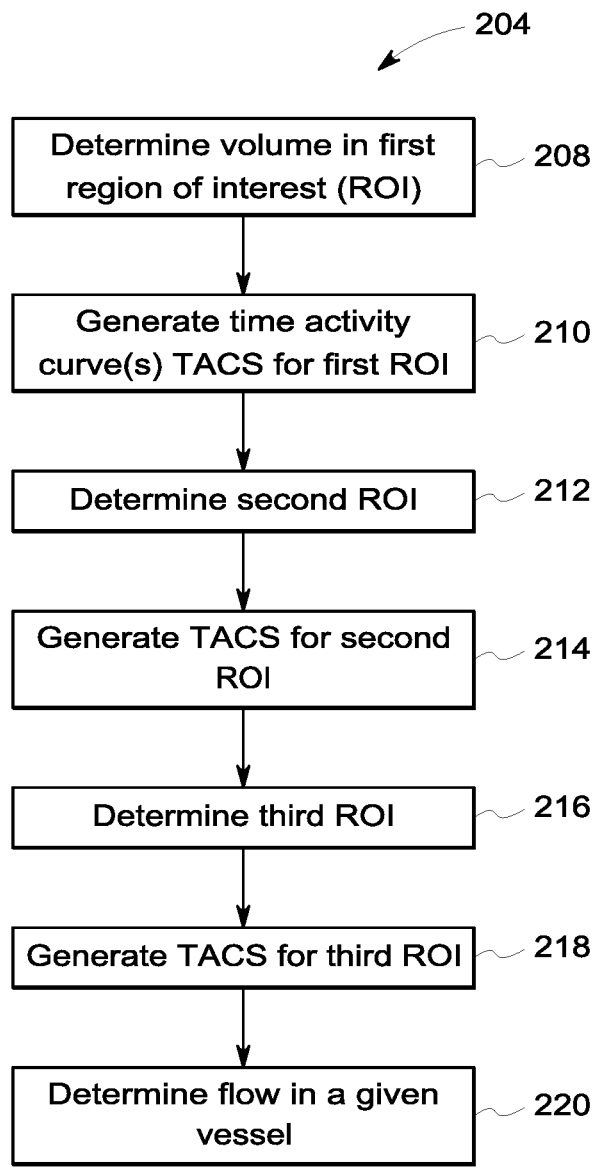
FIG. 11 is a flow chart of a method for determining a flow rate for a given vessel (e.g., rental artery), in accordance with aspects of the disclosed techniques.

FIG. 11 is a flow chart of a method 204 for determining a flow rate for a given vessel (e.g., renal artery). The method 204 expands on blocks 140, 142, and 144 after occurrence of blocks 136 and 138 in the method 134 of FIG. 11. FIG. 12 is a chart 206 for depicting various terms for a multi-term vector from TACs for different regions of interest (i.e., transformations of radiotracer bolus from vein to renal artery) that may be utilized in determining an overall morphology of a radiotracer bolus and a flow for the given vessel. As indicated in the chart 206, injection of tracer into the vein represents a dilution type event, transit through the lungs and heart represents a dilution event, abdominal artery represents a bifurcation type event, and the renal artery represents a bifurcation and narrowing type of event.

Returning to FIG. 11, one or more steps of the method 204 may be performed by the NM multi-head imaging system (e.g., processing unit 120 in FIG. 1) and/or another processing unit. One or more of the steps of the method 204 may be performed at the same time and/or in a different order from that depicted in FIG. 2. The method 204 includes from a point of injection (e.g., vein) to the renal artery (i.e., transformations of radiotracer bolus from vein to renal artery) for reference. One or more steps of the method 204 may be performed by the NM multi-head imaging system (e.g., processing unit 120 in FIG. 1) and/or another processing unit. One or more of the steps of the method 204 may be performed at the same time and/or in a different order from that depicted in FIG. 11. In the following, A represents injected dose, P represents peak of TAC, S represents slope of TAC, T represents duration, and V represents volume. In the following, subscript aa represents abdominal aorta, subscript i represents injection, subscript r represents renal artery, and subscript v represents injected vein. Non-italicized letters represent letters are derived from the TAC for activity and italicized letters represent letters are derived from the TAC for activity divided by volume. The abbreviations mul and div stand for multiply and divide, respectively, and indicate how the terms will be utilized in determining respective flows for different regions of interest.

The method 204 includes determining a volume ($V_v$) under a first region of interest (e.g., of the injected vein) (block 208). Determining the volume includes drawing the region of interest over the injected vein and generating a TAC (block 210). D1 equals $(P_v/V_v)/(A/V_i)$, which is the ratio of concentration of activity in the vein relative to the syringe. A and $V_i$ are injection parameters from the injection of the radiotracer bolus utilizing an automated injector. If a volume of interest can be drawn in the vein, D1 may be determined by $P_v/(A/V_i)$. Flow for the injected vein, $F_v$, equals $(V_i/T_i)$/D1. $T_i$ is also an injection parameter from the injection of the radiotracer bolus utilizing an automated injector. $P_v$ or $P_v$ are from the TAC generated for the first region of interest.

The method 204 also includes determining a second region of interest (e.g., downstream of the site of injection such as the abdominal aorta) (block 212). Upon drawing the second region of interest over the abdominal aorta, the method 204 further includes generating a TAC for the second region of interest (block 214). B3 equals $S_{aa}/S_v$ or $S_{aa}/S_v$. D2 equals $P_{aa}/(P_v \times D1)$ or $P_{aa}/(Pv_v \times D1)$. $S_{aa}$ or $S_{aa}$ and $P_{aa}$ or $P_{aa}$ are from the TAC generated for the second region of interest. $S_v$ or $S_v$ are from the TAC generated for the first region of interest.

The method 204 still further includes determining a third region of interest (e.g., for the given vessel such as the renal artery which is downstream of the other regions of interest) (block 216). Upon drawing the third region of interest over the rental artery, the method 204 yet further includes generating a TAC for the third region of interest (block 218). B4 equals $S_r/S_{aa}$ and N4 equals $P_r/P_{aa}$. $S_r$ and $P_r$ are from the TAC generated for the third region of interest.

The method 204 yet further includes determining the flow or flow rate in the given vessel (e.g., renal artery) (block 220). Determining the flow rate includes estimating the flow for the given vessel based on the morphology of the one or more TACs (e.g., from the TACs generated from the first, second, and third regions of interest) and the injection parameters. In particular, a multi-term vector is utilized for estimating the flow, where the terms of the vector are based on the morphology of the TACs and the injection parameters. The flow rate of the renal artery ($F_r$) equals ($F_v \times B3 \times B4$)/D2. The renal plasma flow or renal blood flow (RBF) equals $F_r$.

Figure 13:
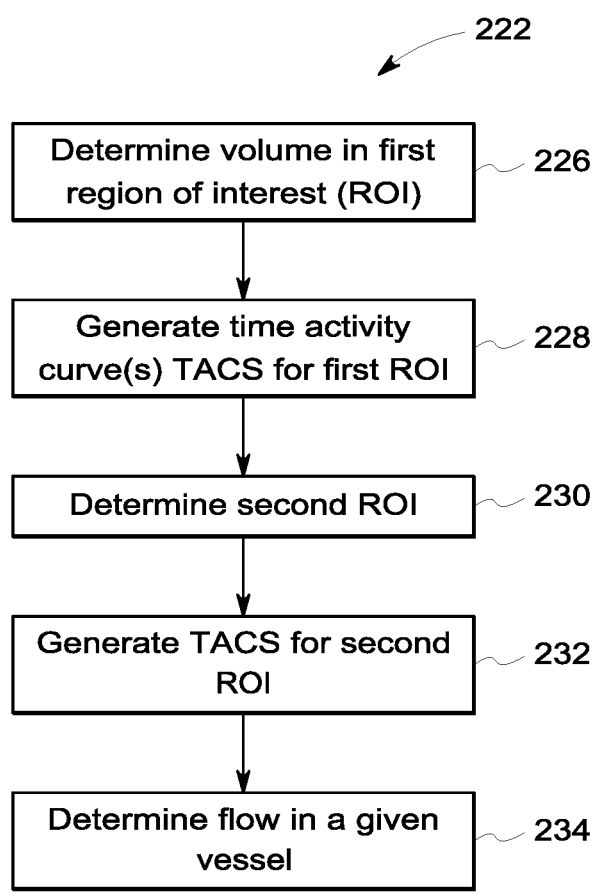
FIG. 13 is a flow chart of another method for determining a flow rate for a given vessel (e.g., rental artery), in accordance with aspects of the disclosed techniques.
Figure 14:
FIG. 14 is a chart depicting various terms from TACs for different regions of interest from a point of injection to the renal artery.

In certain embodiments, a simpler technique may be utilized to determine the flow rate of the given vessel (e.g., renal artery). FIG. 13 is a flow chart of another method 222 for determining a flow rate for a given vessel (e.g., rental artery). The method 222 expands on blocks 140, 142, and 144 after occurrence of blocks 136 and 138 in the method 134 of FIG. 2. FIG. 14 is a chart 224 for depicting various terms for a multi-term vector from TACs for different regions of interest (i.e., transformations of radiotracer bolus from abdominal artery to renal artery) that may be utilized in determining an overall morphology of a radiotracer bolus and a flow for the given vessel. As indicated in the chart 224, the abdominal artery represents a dilution type event and the renal artery represents a bifurcation and narrowing type of event. In both the method 222 and the chart 224, it is assumed that the bolus in the abdominal aorta contains the entire injected activity. As this is not likely, an empirical value may be introduced to estimate the fraction of the cardiac output reaching the abdominal aorta.

Returning to FIG. 13, one or more steps of the method 222 may be performed by the NM multi-head imaging system (e.g., processing unit 120 in FIG. 1) and/or another processing unit. One or more of the steps of the method 222 may be performed at the same time and/or in a different order from that depicted in FIG. 13. The method 222 includes from the abdominal artery to the renal artery (i.e., transformations of radiotracer bolus from vein to renal artery) for reference. One or more steps of the method 222 may be performed by the NM multi-head imaging system (e.g., processing unit 120 in FIG. 1) and/or another processing unit. One or more of the steps of the method 222 may be performed at the same time and/or in a different order from that depicted in FIG. 13. In the following, A represents injected dose, P represents peak of TAC, S represents slope of TAC, T represents duration, and V represents volume. In the following, subscript aa represents abdominal aorta, subscript i represents injection, subscript r represents renal artery, and subscript v represents injected vein. Non-italicized letters represent letters are derived from the TAC for activity and italicized letters represent letters are derived from the TAC for activity divided by volume. The abbreviations mul and div stand for multiply and divide, respectively, and indicate how the terms will be utilized in determining respective flows for different regions of interest.

The method 222 includes determining a volume ($V_{aa}$) under a first region of interest (e.g., abdominal aorta) (block 226). Determining the volume includes drawing the region of interest over the abdominal aorta and generating a TAC (block 228). D1 equals $(P_{aa}/V_{aa})/(A/V_t)$, which is the ratio of concentration of activity in the abdominal aorta relative to the syringe. A and $V_t$ are injection parameters from the injection of the radiotracer bolus utilizing an automated injector. If a volume of interest can be drawn in the artery, D1 may be determined by $(P_{aa}/V_{aa})(A/V_t)$. Flow for the injected vein, $F_{aa}$, equals $(V_t/T_i)/D1$. $T_i$ is also an injection parameter from the injection of the radiotracer bolus utilizing an automated injector. $P_{aa}$ or $P_{aa}$ are from the TAC generated for the first region of interest.

The method 222 also includes determining a second region of interest (e.g., for the given vessel such as the renal artery which is downstream of the other region of interest) (block 230). Upon drawing the second region of interest over the renal artery, the method 204 further includes generating a TAC for the second region of interest (block 232). B2 equals $S_r/S_{aa}$. N2 equals $P_r/P_{aa}$. $P_r$ and $S_r$ are from the TAC generated for the second region of interest. $S_{aa}$ is from the TAC generated for the first region of interest.

The method 222 further includes determining the flow or flow rate in the given vessel (e.g., renal artery) (block 234). Determining the flow rate includes estimating the flow for the given vessel based on the morphology of the one or more TACs (e.g., from the TACs generated from the first and second regions of interest) and the injection parameters. In particular, a multi-term vector is utilized for estimating the flow, where the terms of the vector are based on the morphology of the TACs and the injection parameters. The flow rate of the renal artery ($F_r$) equals $F_{aa} \times B2$. The renal plasma flow or renal blood flow (RBF) equals $F_r$.

With regard to determining GFR, it may be determined without bolus mechanics. If a solute passes the glomeruli freely, GFR can be determined by $(U \times V)/P$, where P represents concentration of solute in plasma (mg/mL), U represents concentration of solute in urine (mg/mL), and V represents volume of urine in an interval of time (mL/min). GFR equals $(A_k \times V_r)/(P_r \times FWHM_r)$. Vr represents the volume of the renal artery, $A_k$ represents the activity in the kidney after bolus transit ($U \times V$), and $P_r/V_r$ represents the activity per mL in the renal artery (P).

Figure 15:
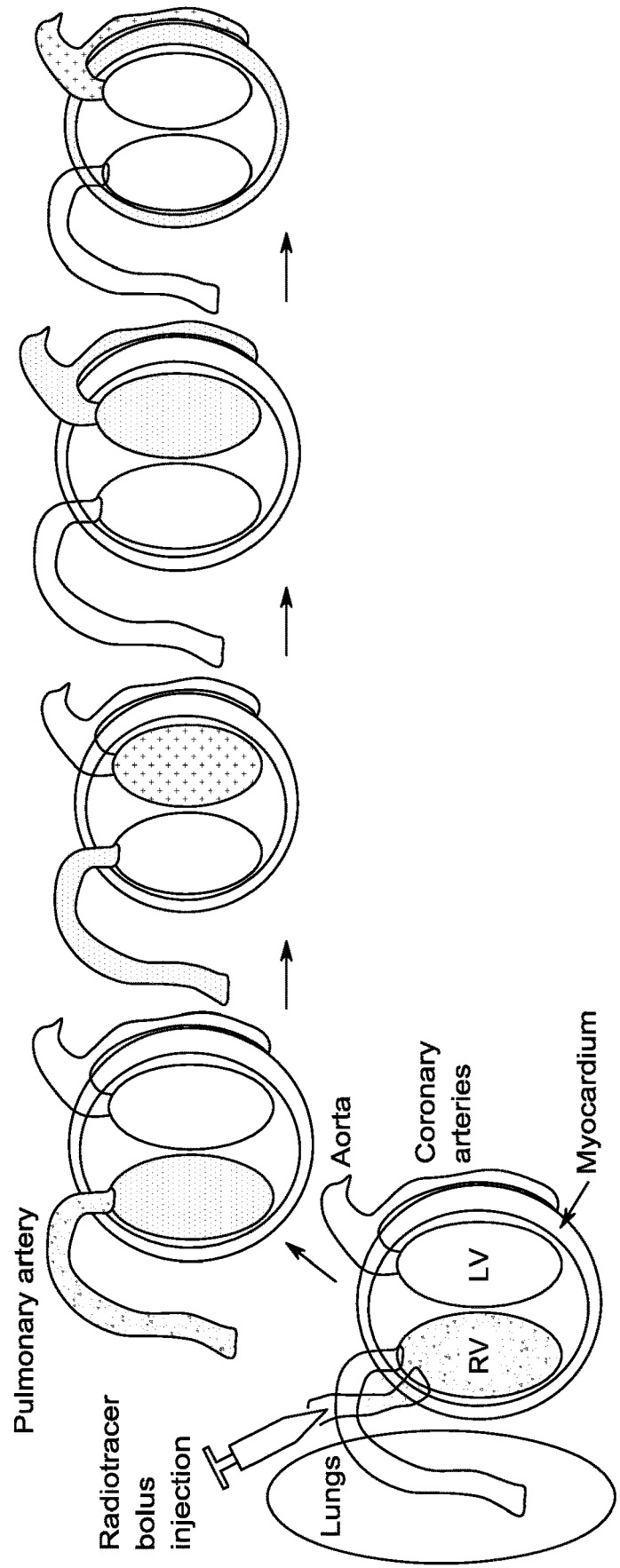
FIG. 15 is a schematic diagram of radiotracer bolus flow through coronary and pulmonary vessels.
Figure 16:
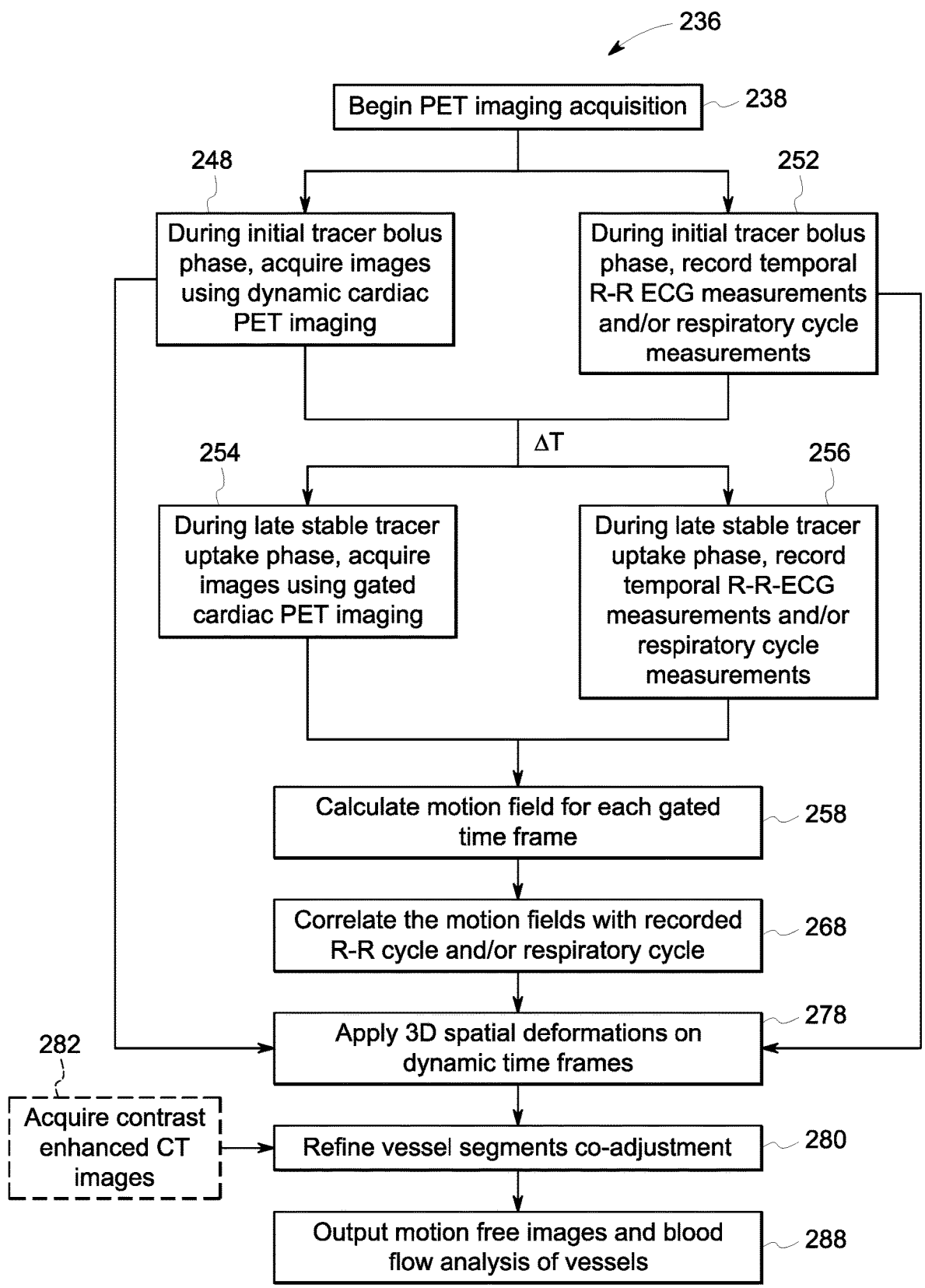
FIG. 16 is a flow chart of a method for determining and visualizing a flow in one or more given vessels (e.g., coronary and/or pulmonary vessels), in accordance with aspects of the disclosed techniques.
Figure 17:
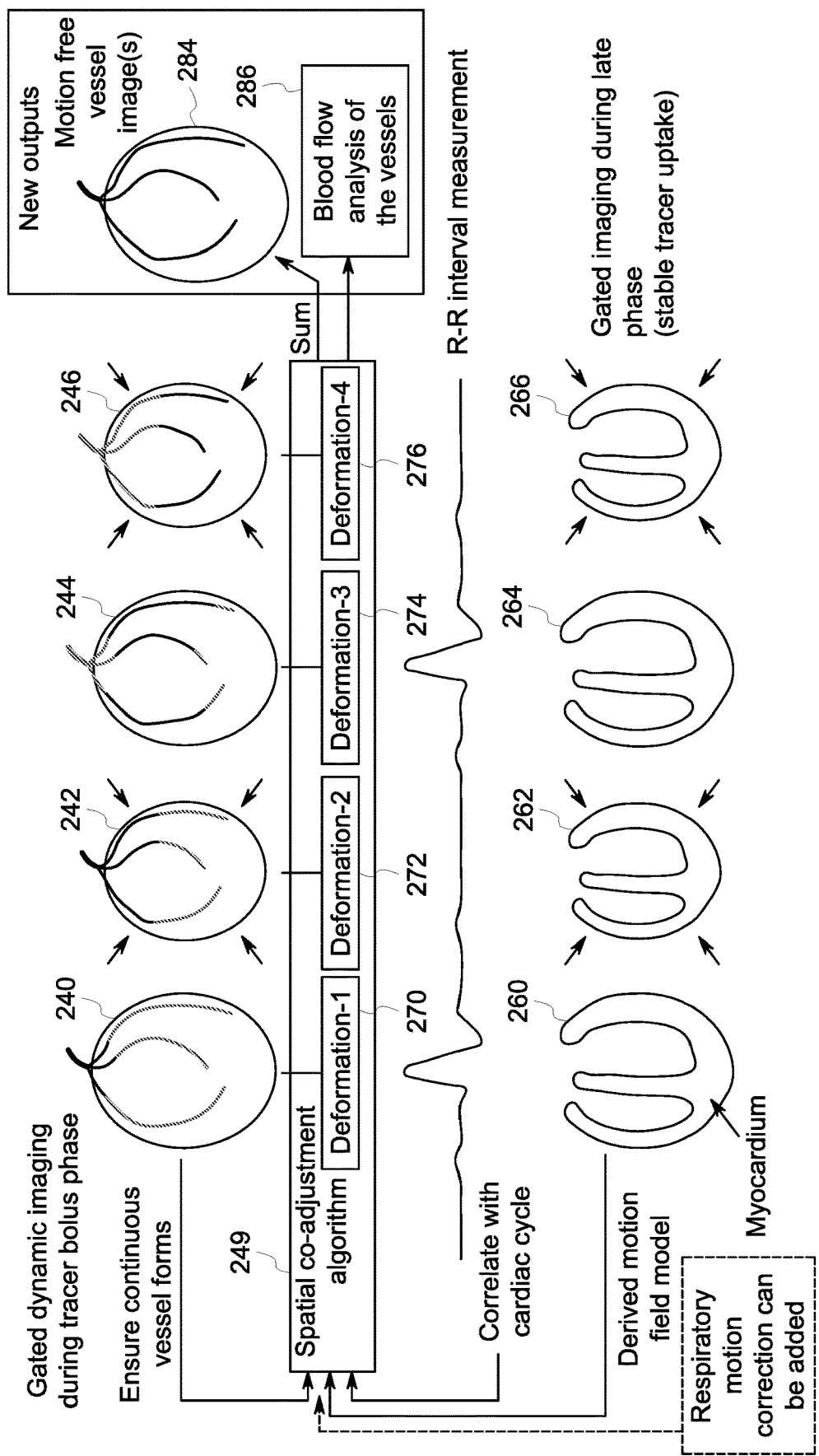
FIG. 17 is a schematic diagram of a method for determining and visualizing a flow in one or more given vessels (e.g., coronary and/or pulmonary vessels), in accordance with aspects of the disclosed techniques.

FIGS. 15-17 provide additional techniques for visualizing and quantifying radiotracer bolus transit through a given vessels or vessels. More specifically, FIGS. 15-17 describe techniques visualizing and quantifying radiotracer bolus transit through coronary vessels or pulmonary vessels utilizing gated dynamic PET or SPECT. Typically, the early dynamic phase of a cardiac PET scan is used primarily for the estimation of the arterial input function for the determination of myocardial blood flow. The embodiments described herein enable the direct visualization and measurement of the flow through the coronary and pulmonary vessels. In particular, the disclosed embodiments include acquiring the initial bolus phase with gated dynamic PET and correcting it for both cardiac and respiratory motion to derive a motion free image on which the bolus transit through the epicardial vessels can be both visually and quantitatively assessed. The disclosed embodiments provide additional information from the cardiac PET scan with no additional radiation and camera time. In addition, the disclosed embodiments avoid invasive coronary angiography, computed tomography angiography, or magnetic resonance imaging that are typically utilized to obtain this additional information.

FIG. 15 is a schematic diagram of radiotracer bolus flow through coronary and pulmonary vessels. As depicted, a radiotracer bolus is injected (e.g., into a vein). During the initial bolus phase, the radiotracer enters the right ventricle and flows into the pulmonary artery and eventually the lungs. From the lungs, the radiotracer enters the left ventricle and flows into the coronary arteries and the aorta and then into the myocardium. As described in greater detail below, gated dynamic PET imaging may be utilized to acquire images of this initial bolus phase (i.e., bolus transit through the pulmonary vessels and the coronary vessels). The coronary arteries can be imaged prior to filling of the myocardium with tracer. In addition, acquiring short time frames enables showing flow progress in the vessels (e.g., pulmonary and coronary vessels). As time progresses during the initial bolus phase and the acquisition of images, cardiac and lung motion occurs that affects the quality of the acquired images. The techniques described below correct for this motion.

FIG. 16 is a flow chart of a method 236 (e.g., spatial co-adjustment algorithm) for determining and visualizing a flow in one or more given vessels (e.g., coronary and/or pulmonary vessels). FIG. 17 is a schematic diagram of the method 236. Returning to FIG. 16, one or more steps of the method 236 may be performed by the NM multi-head imaging system (e.g., processing unit 120 in FIG. 1) and/or another processing unit. One or more of the steps of the method 236 may be performed at the same time and/or in a different order from that depicted in FIG. 16. The method 236 includes beginning a PET imaging acquisition (block 238). After the PET imaging acquisition has begun and a radiotracer bolus subsequently administered to a patient, the method 236 includes, during an initial radiotracer bolus phase, acquiring images (e.g., images 240, 242, 244, and 246 in FIG. 17) of the chest region utilizing gated dynamic cardiac PET imaging (block 248). The images acquired during the dynamic cardiac PET imaging provide continuous vessel forms as an input to a spatial co-adjustment algorithm 249 in FIG. 17. The method 236 also includes, during the initial radiotracer bolus phase, recording temporal R-R ECG interval measurements (e.g., R-R interval measurement 250 in FIG. 17) (block 252). In certain embodiments, during the initial radiotracer bolus phase, respiratory cycle measurements may also be recorded. In certain embodiments, cardiac or respiratory cycle patterns may be derived from the acquired imaging data (e.g., similar to data driven gating).

After the progression of time, the method 236 includes, during the late stable radiotracer uptake phase, acquiring imaging images of the chest region utilizing gated cardiac PET imaging (block 254). The method 236 also includes, during the late stable radiotracer uptake phase, recording temporal R-R ECG interval measurements (block 256). In certain embodiments, during the late stable radiotracer uptake phase, respiratory cycle measurements may also be recorded. In certain embodiments, cardiac or respiratory cycle patterns may be derived from the acquired imaging data (e.g., similar to data driven gating).

The method 236 further includes calculating a motion field model (having transformation matrices to correct motion) for each gated time frame derived from the images acquired during the late stable radiotracer uptake phase (block 258). 3D image registration techniques may be utilized to calculate the motion field models. Examples of motion field models are models 260, 262, 264, and 266 in FIG. 17. The motion field models are provided as inputs to the spatial co-adjustment algorithm 249.

The method 236 still further includes correlating the multiple motion field models with the cardiac R-R cycle record (block 268). In certain embodiments, the multiple motion field models may also be correlated with the respiratory cycle record.

The method 236 yet further includes apply 3D spatial deformations (e.g., deformations 270, 272, 274, and 276 in FIG. 17) on the dynamic time frames (e.g., within the spatial co-adjustment algorithm 249) (block 278). The application of the 3D spatial deformations is based on the calculated motion fields and the matching of the two R-R records (i.e., from the initial radio tracer bolus phase and the late phase stable radiotracer uptake phase). In certain embodiments, the application of the 3D spatial deformations may also be based on matching of the two respiratory cycle records (i.e., from the initial radio tracer bolus phase and the late phase stable radiotracer uptake phase). Besides respiratory gating and cardiac gating, in certain embodiments, breath holding may be utilized in motion correction.

The application of the 3D spatial deformations may provide only a rough continuous-form alignment of the different vessel segments (e.g., coronary or pulmonary vessels) or of the same segment with different tracer signals. In certain embodiments, the method 236 includes refining the vessel segments co-adjustment (block 280). For example, an "optical-flow" algorithm or 3D spatial-registration of local image features which are relevant to the vessel forms may be utilized in the refinement. In certain embodiments, the method 236 includes acquiring contrast enhanced CT images or various MRI images of the chest region that may enable further refining of the vessel PET imaging and the derived quantitative analyses (block 282). In certain embodiments, partial volume correction may be applied utilizing the CT component of the hybrid PET-CT scanner, SPECT-CT scanner or by utilizing MRI components PET-MRI scanner.

The method 236 further includes, upon applying the spatial co-adjustment algorithm to the various inputs, outputting one or more motion free vessel images 284 (see FIG. 17) (of the coronary vessels and/or the pulmonary vessels) and blood flow analysis 286 (see FIG. 17) of the vessels (of the coronary vessels and/or the pulmonary vessels) (block 288). The motion free vessel image is derived from a sum of all local deformations. The steps of the method 236 may be utilized for coronary vessels and/or pulmonary vessels.

Technical effects of the disclosed embodiments enable determining a flow rate for a given vessel (e.g., renal artery) utilizing direct measurement of the bolus morphology for quantitative analysis. Directly measuring the bolus provides a more accurate estimate of the flow in the given vessel. Technical effects of the disclosed embodiments enable direct visualization and quantification of radiotracer bolus transit through a given vessels or vessels (e.g., coronary vessels and/or pulmonary vessels) utilizing gated dynamic PET. The disclosed embodiments provide additional information from the cardiac PET scan with no additional radiation and camera time. In addition, the disclosed embodiments avoid invasive coronary angiography, computed tomography angiography, or magnetic resonance imaging that are typically utilized to obtain this additional information.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112 (f). However, for any claims containing elements designated in any other manner, it is intended that such elements are not to be interpreted under 35 U.S.C. 112 (f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for determining and visualizing flow in one or more given vessels, comprising:
    acquiring, via a processor during an initial radiotracer bolus phase, images of a chest region of a subject utilizing gated dynamic cardiac emission tomography imaging;
    recording, via the processor during the initial radiotracer bolus phase, temporal R-R electrocardiogram interval measurements and/or respiratory cycle measurements of the subject;
    acquiring, via a processor during a late stable tracer uptake phase, additional images of the chest region of the subject utilizing gated cardiac emission tomography imaging;
    recording, via the processor during the late stable tracer uptake phase, additional temporal R-R electrocardiogram interval measurements and/or additional respiratory cycle measurements of the subject;
    calculating, via the processor, a respective motion field model for each gated time frame derived from the additional images, wherein each respective motion field model comprises transformation matrices to correct motion;
    correlating, via the processor, each of the respective motion field models to the additional temporal R-R electrocardiogram interval measurements and/or the additional respiratory cycle measurements;
    applying, via the processor, three-dimensional (3D) spatial deformations on each dynamic time frame derived from the images; and
    outputting, via the processor, one or more motion free images of the one or more given vessels and blood flow analysis of the one or more given vessels.

2. The computer-implemented method of claim 1, wherein applying the 3D spatial deformations on each dynamic time frame is based on both the respective motion field model and matching between the temporal R-R electrocardiogram interval measurements and/or the respiratory cycle measurements and the additional temporal R-R electrocardiogram interval measurements and/or the additional respiratory cycle measurements, respectively.

3. The computer-implemented method of claim 1, further comprising, prior to outputting the one or more motion free images and the blood flow analysis of the one or more given vessels, refining, via the processor, co-adjustment of vessel segments of the one or more given vessels.

4. The computer-implemented method of claim 3, wherein refining co-adjustment of the vessel segments comprises refining co-adjustment of the vessel segments via an optical flow algorithm or 3D spatial-registration of local image features relevant to vessel forms of the one or more given vessels.

5. The computer-implemented method of claim 3, wherein refining co-adjustment of the vessel segments comprises refining co-adjustment of the vessel segments utilizing contrast enhanced computed tomography images acquired of the one or more given vessels.

6. The computer-implemented method of claim 1, wherein each motion free image of the one or more motion free images is derived from a sum of all local transformations.

7. The computer-implemented method of claim 1, wherein calculating the respective motion field model for each gated time frame derived from the additional images comprises calculating the respective field model for each gated time frame utilizing 3D registration.

8. One or more non-transitory computer-readable media encoding one or more processor-executable routines, wherein the one or more processor-executable routines, when executed by a processor, cause acts to be performed comprising:
   acquiring, during an initial radiotracer bolus phase, images of a chest region of a subject having one or more given vessels utilizing gated dynamic cardiac emission tomography imaging;
   recording, during the initial radiotracer bolus phase, temporal R-R electrocardiogram interval measurements and/or respiratory cycle measurements of the subject;
   acquiring, during a late stable tracer uptake phase, additional images of the chest region of the subject utilizing gated cardiac emission tomography imaging;
   recording, during the late stable tracer uptake phase, additional temporal R-R electrocardiogram interval measurements and/or additional respiratory cycle measurements of the subject;
   calculating a respective motion field model for each gated time frame derived from the additional images, wherein each respective motion field model comprises transformation matrices to correct motion;
   correlating each of the respective motion field models to the additional temporal R-R electrocardiogram interval measurements and/or the additional respiratory cycle measurements;
   applying three-dimensional (3D) spatial deformations on each dynamic time frame derived from the images; and
   outputting one or more motion free images of the one or more given vessels and blood flow analysis of the one or more given vessels.

9. The one or more non-transitory computer-readable media of claim 8, wherein applying the 3D spatial deformations on each dynamic time frame is based on both the respective motion field model and matching between the temporal R-R electrocardiogram interval measurements and/or the respiratory cycle measurements and the additional temporal R-R electrocardiogram interval measurements and/or the additional respiratory cycle measurements, respectively.

10. The one or more non-transitory computer-readable media of claim 8, wherein the acts further comprise, prior to outputting the one or more motion free images and the blood flow analysis of the one or more given vessels, refining co-adjustment of vessel segments of the one or more given vessels.

11. The one or more non-transitory computer-readable media of claim 10, wherein refining co-adjustment of the vessel segments comprises refining co-adjustment of the vessel segments via an optical flow algorithm or 3D spatial-registration of local image features relevant to vessel forms of the one or more given vessels.

12. The one or more non-transitory computer-readable media of claim 10, wherein refining co-adjustment of the vessel segments comprises refining co-adjustment of the vessel segments utilizing contrast enhanced computed tomography images acquired of the one or more given vessels.

13. The one or more non-transitory computer-readable media of claim 8, wherein each motion free image of the one or more motion free images is derived from a sum of all local transformations.

14. The one or more non-transitory computer-readable media of claim 8, wherein calculating the respective motion field model for each gated time frame derived from the additional images comprises calculating the respective field model for each gated time frame utilizing 3D registration.

15. A processor-based system for determining and visualizing flow in one or more given vessels, comprising:
   a memory encoding one or more processor-executable routines, wherein the one or more processor-executable routines, when executed cause acts to be performed comprising:
      acquiring, during an initial radiotracer bolus phase, images of a chest region of a subject having one or more given vessels utilizing gated dynamic cardiac emission tomography imaging;
      recording, during the initial radiotracer bolus phase, temporal R-R electrocardiogram interval measurements and/or respiratory cycle measurements of the subject;
      acquiring, during a late stable tracer uptake phase, additional images of the chest region of the subject utilizing gated cardiac emission tomography imaging;
      recording, during the late stable tracer uptake phase, additional temporal R-R electrocardiogram interval measurements and/or additional respiratory cycle measurements of the subject;
      calculating a respective motion field model for each gated time frame derived from the additional images, wherein each respective motion field model comprises transformation matrices to correct motion;
      correlating each of the respective motion field models to the additional temporal R-R electrocardiogram interval measurements and/or the additional respiratory cycle measurements;
      applying three-dimensional (3D) spatial deformations on each dynamic time frame derived from the images; and
      outputting one or more motion free images of the one or more given vessels and blood flow analysis of the one or more given vessels; and
   a processor configured to access and execute the one or more processor-executable routines encoded by the memory.

16. The processor-based system of claim 15, wherein applying the 3D spatial deformations on each dynamic time frame is based on both the respective motion field model and matching between the temporal R-R electrocardiogram interval measurements and/or the respiratory cycle measurements and the additional temporal R-R electrocardiogram interval measurements and/or the additional respiratory cycle measurements, respectively.

17. The processor-based system of claim 15, further comprising, prior to outputting the one or more motion free images and the blood flow analysis of the one or more given vessels, refining co-adjustment of vessel segments of the one or more given vessels.

18. The processor-based system of claim 17, wherein refining co-adjustment of the vessel segments comprises refining co-adjustment of the vessel segments via an optical flow algorithm or 3D spatial-registration of local image features relevant to vessel forms of the one or more given vessels.

19. The processor-based system of claim 17, wherein refining co-adjustment of the vessel segments comprises refining co-adjustment of the vessel segments utilizing contrast enhanced computed tomography images acquired of the one or more given vessels.

20. The processor-based system of claim 15, wherein the gated dynamic cardiac emission tomography imaging comprises gated dynamic cardiac positron emission tomography imaging and gated cardiac emission tomography imaging comprises gated cardiac positron emission tomography imaging.

* * * * *